US012799526B2

(12) United States Patent
Peng et al.

(10) Patent No.: US 12,799,526 B2
(45) Date of Patent: Nov. 17, 2026

(54) ANTIGEN SPECIFIC TCR IDENTIFICATION USING SINGLE-CELL SORTING

(71) Applicant: ADOC SSF, LLC, South San Francisco, CA (US)

(72) Inventors: Songming Peng, San Mateo, CA (US); Alex Franzusoff, El Granada, CA (US)

(73) Assignee: ADOC SSF, LLC, South San Francisco, CA (US)

(*) Notice: Subject to any disclaimer, the term of this patent is extended or adjusted under 35 U.S.C. 154(b) by 1129 days.

(21) Appl. No.: 17/202,067

(22) Filed: Mar. 15, 2021

(65) Prior Publication Data

US 2021/0230544 A1 Jul. 29, 2021

Related U.S. Application Data

(63) Continuation of application No. PCT/US2019/050865, filed on Sep. 12, 2019.

(60) Provisional application No. 62/731,013, filed on Sep. 13, 2018.

(51) Int. Cl.

| | |
|---|---|
| ***C12Q 1/6844*** | (2018.01) |
| ***A61K 40/11*** | (2025.01) |
| ***A61K 40/32*** | (2025.01) |
| ***A61K 40/42*** | (2025.01) |
| ***C12N 5/0783*** | (2010.01) |
| ***C12Q 1/6874*** | (2018.01) |

(52) U.S. Cl.

CPC ............ *C12Q 1/6844* (2013.01); *A61K 40/11* (2025.01); *A61K 40/32* (2025.01); *A61K 40/4201* (2025.01); *C12N 5/0636* (2013.01); *C12Q 1/6874* (2013.01)

(58) Field of Classification Search

CPC ......................... C12N 5/0636; C12N 15/1037; C12Q 1/6874; C12Q 1/6844; A61K 39/464401; A61K 40/32; A61K 40/4201; A61K 40/11

See application file for complete search history.

(56) References Cited

U.S. PATENT DOCUMENTS

| | | | | |
|---|---|---|---|---|
| 7,807,377 | B2 | 10/2010 | Albani | |
| 9,115,402 | B2 | 8/2015 | Hacohen et al. | |
| 10,481,158 | B2 * | 11/2019 | Heath | G01N 15/14 |
| 2002/0151690 | A1 | 10/2002 | Luxemburg et al. | |
| 2003/0003535 | A1 | 1/2003 | Reiter | |
| 2004/0180346 | A1 | 9/2004 | Anderson et al. | |
| 2006/0079583 | A1 | 4/2006 | Higuchi et al. | |
| 2006/0079584 | A1 | 4/2006 | Higuchi et al. | |
| 2008/0219947 | A1 | 9/2008 | Linette et al. | |
| 2009/0117153 | A1 | 5/2009 | Hansen et al. | |
| 2009/0235990 | A1 | 9/2009 | Beer | |
| 2010/0021984 | A1 | 1/2010 | Edd et al. | |
| 2015/0329617 | A1 | 11/2015 | Winther et al. | |
| 2015/0376609 | A1 | 12/2015 | Hindson et al. | |
| 2017/0003288 | A1 * | 1/2017 | Heath | G01N 33/56972 |
| 2017/0199961 | A1 | 7/2017 | Yelensky et al. | |
| 2017/0343545 | A1 * | 11/2017 | Hadrup | C07K 19/00 |
| 2020/0309765 | A1 * | 10/2020 | Bethune | G01N 33/566 |
| 2023/0069843 | A1 * | 3/2023 | Heath | B01L 3/502761 |

FOREIGN PATENT DOCUMENTS

| | | | |
|---|---|---|---|
| WO | WO 2018/085453 | A1 | 5/2018 |
| WO | WO 2018/165475 | A1 | 9/2018 |
| WO | WO 2019/023269 | A1 | 1/2019 |

OTHER PUBLICATIONS

Bentzen et al. (Cancer Immunol Immunother . May 2017;66(5):657-666. doi: 10.1007/s00262-017-1971-5. Epub Mar. 17, 2017.) ( Year: 2017).*

Altschul et al., "Basic Local Alignment Search Tool," J. Mol Biol. 215:403-410 (1990).

Bakker et al., "Conditional MHC class I ligands and peptide exchange technology for the human MHC gene products HLA-A1, -A3, -A11, and -B7," PNAS 105(10):3825-3830 (2008).

Bardi et al., "HLA-A, B and DRB1 allele and haplotype frequencies in volunteer bone marrow donors from the north of Parana State," Rev Bras Hematol Hemoter. 34(1):25-30 (2012).

Bethune et al., "Preparation of peptide-MHC and T-cell receptor dextramers by biotinylated dextran doping," BioTechniques 62:123-130 (2017).

Fritsch et al., "HLA-Binding Properties of Tumor Neoepitopes in Humans," Cancer Immunol Res 2(6):522-529 (2014).

http://www.idtdna.com/pages/education/decoded/article/which-biotin-modification-to-use-> (Received Mar. 1, 2018).

International Search Report mailed Nov. 26, 2019 in International Application No. PCT/US2019/050865.

Islam et al., "Quantitative single-cell RNA-seq with unique molecular identifiers," Nature Methods 11(2):163-166 (2014).

Needleman et al., "A General Method Applicable to the Search for Similarities in the Amino Acid Sequence of Two Proteins," J. Mol. Biol. 48:443-453 (1970).

Novak et al., "MHC class II tetramers identify peptide-specific human CD4+ T cells proliferating in response to influenza A antigen," J. Clin. Invest 104(12):R63-R67 (1999).

Pearson et al., "Improved tools for biological sequence comparison," Proc. Nat'l. Acad. Sci. USA 85:2444-2448 (1988).

Peng et al., "Sensitive, Non-Destructive Detection and Analysis of Neoantigen-Specific T Cell Populations from Tumors and Blood," Cell Press Sneak Peak, Apr. 12, 2018, pp. 1-46.

Smith et al., "Comparison of Biosequences," Adv. Appl. Math. 2:482-489 (1981).

Toebes et al., "Generation of antigen-specific T cell immunity through T cell receptor gene transfer," Nat. Med 12:246-251 (2006).

* cited by examiner

*Primary Examiner* — Fereydoun G Sajjadi
*Assistant Examiner* — Joel D Levin
(74) *Attorney, Agent, or Firm* — Baker Botts L.L.P.

(57) ABSTRACT

Compositions and methods for identifying antigen-specific T cells, including determining paired T cell receptor sequences for a specific antigen, are described. Compositions and methods for identifying neoantigen-specific T cells are also described.

15 Claims, 7 Drawing Sheets

Specification includes a Sequence Listing.

| [illegible] | i701 | i702 | i703 | i704 | i705 | i706 | i707 | i708 | i709 | i710 | i711 | i712 |
|---|---|---|---|---|---|---|---|---|---|---|---|---|
| i501 | A1 | | | | | | | | | | | |
| i502 | | | | | | | | | | | | |
| i503 | | | C3 | | | | | | | | | |
| i504 | | | | | | | | | | | | |
| i505 | | | | | | | | | | | | |
| i506 | | | | | | | | | | | | |
| i507 | | | | | | | | | | | | |
| i508 | | | | | | | | | | | | |

SEQUENCE LISTING

<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: peptide

<400> SEQUENCE: 1

Asn Leu Val Pro Met Val Ala Thr Val
1 5

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: biotinylation motif

<400> SEQUENCE: 2

Gly Leu Asn Asp Ile Phe Glu Ala Gln Lys Ile Glu Trp His Glu
1 5 10 15

ANTIGEN SPECIFIC TCR IDENTIFICATION USING SINGLE-CELL SORTING

CROSS REFERENCE TO RELATED APPLICATIONS

This application is a Continuation of International Patent Application No. PCT/US2019/050865, filed on Sep. 12, 2019, which claims the benefit of U.S. Provisional Application No. 62/731,013, filed Sep. 13, 2018, each of which is hereby incorporated in its entirety by reference for all purposes.

SEQUENCE LISTING

The instant application contains a Sequence Listing which has been submitted via EFS-Web and is hereby incorporated by reference in its entirety. Said ASCII copy, created on Mar. 15, 2021, is named 0875200178_SL.txt, and is 797 bytes in size.

BACKGROUND

An outstanding challenge in immunology is that of matching, for a given T cell, the T cell receptor (TCR) sequence with the antigen-specificity of that T cell. The T cell receptor gene of many T cells is a heterodimeric protein, with two components-alpha (c) and beta (β) chains. Similar to antibodies, these two chains have a constant region and a variable region. If T cells are collected from a patient, generally each individual T cell has a unique TCR gene that enables that T cell to recognize a unique antigen.

Pairing the antigen specificity of a T cell with the TCR gene is informative and useful. For example, knowledge of the antigens that a T cell subset recognizes can guide the design of therapy. Likewise, knowledge of TCR genes can guide the design of an engineered cell-based therapy. However, previous approaches for antigen-specific T cell pairing have shown to be laborious, non-quantitative, and/or they may only identify one or two T cell populations per HLA genotype due to limited sensitivity. Thus, the ability to analyze TCR antigen specificity at the single cell level remains a significant need in the field.

SUMMARY

Disclosed herein is a method for isolating an antigen specific T cell, the method comprising the steps of: a) providing a composition comprising: 1) an MHC display moiety comprising at least one antigenic peptide; 2) a unique, defined polynucleotide barcode sequence, wherein the defined polynucleotide barcode sequence is operably associated with the identity of the antigenic peptide; and 3) at least one particle; wherein the MHC display moiety and the defined polynucleotide barcode sequence are attached, with or without a linker, to the at least one particle; b) providing a sample known or suspected to comprise one or more T cells; c) contacting the composition with the sample, wherein the contacting comprises providing conditions sufficient for a single T cell to bind the MHC display moiety attached to the at least one particle, and d) isolating a single antigen specific T cell associated with the at least one particle.

In some embodiments, the isolating comprises using fluorescence-activated cell sorting (FACS). In some embodiments, the isolating step comprises using a microfluidic device. In some embodiments, the microfluidic device comprises a flow cytometer.

In some embodiments, the isolating step comprises isolating the single T cell in a single reaction vessel. In some embodiments, the single reaction vessel is an individual well.

In some embodiments, the method further comprises adding a lysis reagent. In some embodiments, the method further comprises adding a RNA reverse transcriptase. In some embodiments, the method further comprises adding a DNA polymerase. In some embodiments, the method further comprises adding dithiothreitol (DTT). In some embodiments, the method further comprises adding additional components for nucleic acid amplification, wherein the additional components are selected from the group consisting of: dNTPs, DNase inhibitors, RNase inhibitors, buffering agents, chelators, divalent ions, and combinations thereof.

In some embodiments, the method further comprises adding: a) a TCRα forward primer, the TCRα forward primer comprising a sequence designed to hybridize to a TCRα variable region sequence; and b) a TCRβ forward primer, the TCRβ forward primer comprising a sequence designed to hybridize to a known TCRβ variable region sequence. In some embodiments, the TCRα forward primer and TCRβ forward primer are designed to amplify at least a portion of a TCR complementarity determining region (CDR) 3 sequence. In some embodiments, the TCRα forward primer and TCRβ forward primer comprise TCRα multiplexed primers and TCRβ multiplexed primers.

In some embodiments, the method further comprises generating or having generated a cDNA mixture, wherein the generating comprises reverse transcription, and the resulting cDNA mixture comprises a sequence complementary to the TCRα RNA transcript and a sequence complementary to the TCRβ RNA transcript.

In some embodiments, the method further comprises an amplification step, the step comprising: i) contacting the resulting cDNA mixture with a forward amplification primer; ii) contacting the resulting cDNA mixture with a reverse amplification primer; iii) performing a DNA amplification to produce an amplified cDNA mixture; and iv) optionally, purifying the amplified cDNA mixture. In some embodiments, the amplification step further comprises contacting the resulting cDNA mixture with a reaction vessel-specific barcode. In some embodiments, the reaction vessel-specific barcode comprises a well-specific barcode. In some embodiments, the reaction vessel-specific barcode comprises a pair of reaction vessel-specific barcodes. In some embodiments, the reaction vessel-specific barcode is operatively linked to each cDNA species in the amplified cDNA mixture.

In some embodiments, the purifying comprises isolating the cDNA mixture on an agarose gel.

In some embodiments, the method further comprises sequencing or having sequenced the cDNA mixture. In some embodiments, the sequencing comprises next generation sequencing.

In some embodiments, the method further comprises assigning or having assigned a paired TCRα sequence and TCR β sequence to the at least one antigenic peptide associated with the single T cell using the defined polynucleotide barcode sequence In some embodiments, the antigen specific T cell is selected from the group consisting of: a primary T cell, an ex vivo cultured T cell, a tumor infiltrating T cell, and an engineered T cell.

In some embodiments, the sample is selected from the group consisting of: blood, plasma, a peripheral blood mononuclear cell population, a tissue homogenate, a tumor homogenate, and an ex vivo T cell culture.

In some embodiments, the at least one particle is selected from the group consisting of: a surface, a nanoparticle, a bead, and a polymer. In some embodiments, the polymer is a dextran particle. In some embodiments, the MHC display moiety comprises three copies of a biotinylated MHC bound to a streptavidin core through a biotin-streptavidin interaction, and wherein the streptavidin core is bound to the dextran particle through a biotin-streptavidin interaction. In some embodiments, the defined polynucleotide barcode sequence comprises three copies of the defined polynucleotide barcode sequence bound to a streptavidin core through a biotin-streptavidin interaction, and wherein the streptavidin core is bound to the dextran particle through a biotin-streptavidin interaction.

In some embodiments, the nanoparticle is a magnetic nanoparticle or a polystyrene nanoparticle. In some embodiments, the bead is an agarose bead or a sepharose bead.

In some embodiments, the composition further comprises a fluorophore.

In some embodiments, the at least one antigenic peptide is selected from the group consisting of: a tumor antigen, a neoantigen, a tumor neoantigen, a viral antigen, a phosphoantigen, a bacterial antigen, a microbial antigen, and combinations thereof. In some embodiments, the at least one antigenic peptide is a neoantigen. In some embodiments, the neoantigen is selected by analyzing tumor, viral, or bacterial sequencing data from a subject to identify one or more somatic mutations. In some embodiments, the analyzing is performed using an in silico predictive algorithm. In some embodiments, the predictive algorithm comprises an MHC binding algorithm to predict binding between the neoantigen and a MHC allele of the subject. In some embodiments, the MHC display moiety is the MHC allele of the subject.

In some embodiments, the MHC display moiety comprises a mammalian MHC. In some embodiments, the mammalian MHC comprises a human MHC. In some embodiments, the mammalian MHC comprises a MHC class I molecule. In some embodiments, the MHC class I molecule comprises a MHC molecule selected from the group consisting of: HLA-A, HLA-B, and HLA-C. In some embodiments, the at least one antigenic peptide is 7-15, 7-10, 8-9, 7, 8, 9, 10, 11, 12, 13, 14, or 15 amino acids in length. In some embodiments, the at least one antigenic peptide is between 8-10 amino acids in length.

In some embodiments, the mammalian MHC comprises a MHC class II molecule. In some embodiments, the MHC class II molecule comprises and MHC molecule selected from the group consisting of: HLA-DQ and HLA-DR. In some embodiments, the at least one antigenic peptide is 11-30, 14-20, 15-18, 11, 12, 13, 14, 15, 16, 17, 18, 19, 20, 21, 22, 23, 24, 25, 26, 27, 28, 29, or 30 amino acids in length. In some embodiments, the at least one antigenic peptide is between 10 and 35, between 10 and 30, between 10 and 25, or between 10 and 20 amino acids in length.

In some embodiments, the MHC display moiety comprises a multimerized MHC. In some embodiments, the multimerized MHC comprises a streptavidin core bound to multiple MHCs. In some embodiments, the streptavidin core further comprises a fluorescent molecule. In some embodiments, the streptavidin core is bound to four copies of a biotinylated MHC. In some embodiments, the MHC display moiety comprises a single chain trimer MHC. In some embodiments, the single chain trimer comprises a disulfide trap.

In some embodiments, the defined barcode polynucleotide sequence is between 4-10 nucleotides in length. In some embodiments, the defined barcode polynucleotide sequence is about 6 nucleotides in length.

Also described herein is a method of treatment for a subject in need thereof, the method comprising administering a therapeutically effective amount of treatment comprising the paired TCRα sequence and TCR β sequence identified using the methods in any one of the methods described herein.

Also described herein is a library comprising: a) two or more distinct particles, each distinct particle comprising: 1) an MHC display moiety comprising at least one antigenic peptide; 2) a unique, defined polynucleotide barcode sequence, wherein the defined polynucleotide barcode sequence is operably associated with the identity of the antigenic peptide; wherein the MHC display moiety and the defined polynucleotide barcode sequence are attached, with or without a linker, to each distinct particle, each distinct particle comprises a unique antigen, and the unique, defined barcode sequence attached to each distinct particle is operably associated with the identity of each unique antigen. In some embodiments, the library composition further comprises a fluorophore, wherein the fluorophore is attached to each distinct particle. In some embodiments, the library composition further comprises two or more distinct fluorophores, wherein a distinct fluorophore of the two or more distinct fluorophores is attached to each distinct particle. In some embodiments, the library composition further comprises two or more distinct fluorophores, wherein two distinct fluorophores of the two or more distinct fluorophores are each separately attached to a distinct population of each distinct particle.

Also described herein is a method for isolating an antigen specific T cell, the method comprising the steps of: a) providing any of the library compositions described herein; b) providing a sample known or suspected to comprise one or more T cells; c) contacting the library composition with the sample, wherein the contacting comprises providing conditions sufficient for a single T cell to bind the MHC display moiety attached at least one of the two or more distinct particles, and d) isolating a single antigen specific T cell associated with the at least one of the two or more distinct particles.

BRIEF DESCRIPTION OF THE SEVERAL VIEWS OF THE DRAWINGS

These and other features, aspects, and advantages of the present invention will become better understood with regard to the following description, and accompanying drawings, where:

As shown in FIG. 1, both the DNA barcodes (2) and the MHC trimers (1) are bound to separate and distinct streptavidin cores. (1)-(4) refer to the elements identified in the figure.

DETAILED DESCRIPTION OF THE INVENTION

Figure 1:
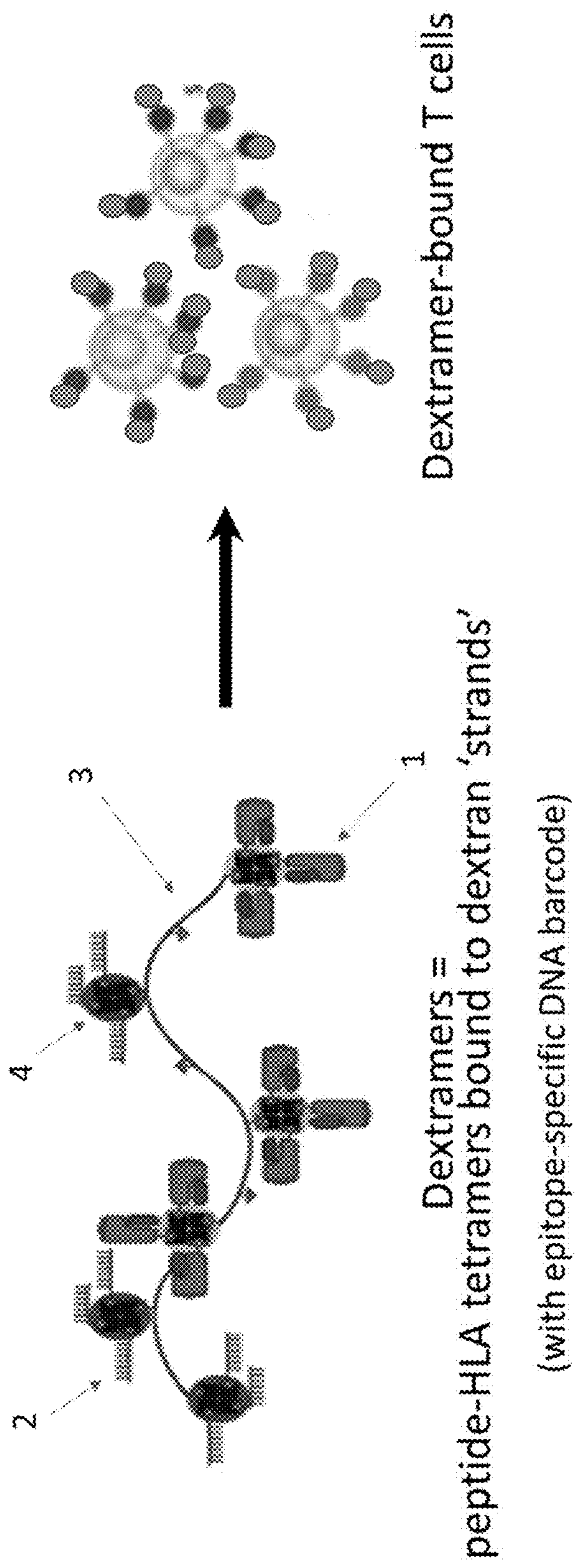
FIG. 1 illustrates a dextramer MHC library element design for capturing antigen-specific cytotoxic T cells (CTLs). The dextramers (also referred to as MHC dextramers) shown in FIG. 1 comprise a peptide-HLA tetramer bound to dextran strands and epitope-specific DNA barcodes. Each dextramer MHC is composed of three pieces: (a) a biotinylated DNA barcode trimer with a streptavidin core (see (2) for the DNA barcode and (4) for the streptavidin core); (b) a biontinylated MHC-antigen trimer with a streptavidin core (1, pointing to a single unit of the trimer); (c) a biotinylated dextran (3) that binds to the streptavidin core of the DNA barcode (2) and MHC trimers (1).

The details of various embodiments of the invention are set forth in the description below. Other features, objects, and advantages of the invention will be apparent from the description and the drawings, and from the claims.

Definitions

Terms used in the claims and specification are defined as set forth below unless otherwise specified.

As used herein, "antigen-specific T cells" refer to cells that are distinguished from one another by their T cell receptors (TCRs), which give them their antigen specificity.

Embodiments of the present invention include a recombinant antigen-MHC complex that is capable of pairing with cognate T cells. As used herein, "antigen complex," "antigen-MHC," "antigen-MHC complex," "recombinant antigen-MHC complex," "peptide MHC," and "p/MHC," are used interchangeably to refer to a recombinant major histocompatibility complex with a peptide in the antigen binding groove.

As used herein, "antigen" includes any antigen including patient-specific neoantigens.

The term "ameliorating" refers to any therapeutically beneficial result in the treatment of a disease state, e.g., a cancerous disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih-.gov/).

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease.

It must be noted that, as used in the specification and the appended claims, the singular forms "a," "an" and "the" include plural referents unless the context clearly dictates otherwise.

INTRODUCTION

T-cell mediated immunity can be characterized by the activation of antigen-specific cytotoxic T cells that are able to induce death in cells that display antigen in a major histocompatibility complex (MHC) on their surface. These cells can display an MHC complex loaded with antigen including virus-infected cells, cells with intracellular bacteria, cells that have internalized or phagocytosed extracellular sources of protein, and cancer cells displaying tumor antigens.

To utilize the T-cell mediated immunity process, e.g., for patient-specific cancer immunotherapy, one of the initial steps can include identification of the patient's tumor-specific antigens (e.g., neoantigens). For identification of a patient's putative neoantigens (tumor or pathogen), in silico predictive algorithmic programs can be utilized that analyze the tumor, viral, or bacterial sequencing data including whole genome, whole exome, or transcriptome sequencing data, to identify one or more mutations corresponding to putatively expressed neoantigens. Additionally, human leukocyte antigen (HLA) typing can be determined from a tumor or blood sample of the patient, and this HLA information can be utilized together with the identified putative neoantigen peptide sequences in a predictive algorithm for MHC binding, as verified by Fritsch et al., 2014, *Cancer Immunol Res.,* 2:522-529, the entire contents of which are herein incorporated by reference. HLAs commonly found in the human population can also be included in neoantigen prediction algorithms, such as HLA-A*02, 24, 01; HLA-B*35, 44, 51; DRB1*11, 13, 07 in caucasians, HLA-A*02, 03, 30; HLA-B*35, 15, 44; DRB1*13, 11, 03 in afro-brazialians, and HLA-A*24, 02, 26; HLA-B*40, 51, 52; DRB1*04, 15, 09 in Asians. Specific pairing of HLA alleles can also be used. Common alleles found in the human population is further described in Bardi et al. (Rev Bras Hematol Hemoter. 2012; 34(1): 25-30), herein incorporated by reference for all it teaches.

Additional examples of methods to identify neoantigens include combining sequencing with mass-spectrometry and MHC presentation prediction (e.g., US Publication No. 2017/0199961), and combining sequencing with MHC binding affinity prediction (e.g., issued U.S. Pat. No. 9,115,402). In addition, methods useful for identifying whether neoantigen specific T cells are present in a patient sample can be used in combination with the methods described here, e.g., as described in US Publication No. 2017/0003288 and PCT/US17/59598, herein incorporated by reference in their entirety. These analyses result in a ranked list of the patient's candidate neoantigen peptides which can be readily synthesized using routine methods for screening of cognate antigen-specific T cells.

Embodiments include using antigen-loaded MHC compositions for isolation and identification of patient-specific T cell populations targeted to patient-specific antigens, e.g., neoantigens. Specifically, the specific TCRα and TCRβ chains expressed in a single antigen specific T cell are determined allowing identification of a TCR that specifically recognizes a given antigen-MHC complex. As described herein, a particle attached to an antigen-MHC complex displaying a unique antigen can be used to identify antigen specific T cells. For example, following antigen specific recognition, a T cell and barcoded particle-antigen-MHC bind to create a barcoded T cell. Utilizing the properties of the particle, such as fluorescence, barcoded T cells that pair with the antigen-MHC complex can be isolated by selective isolation of the particle into single-cell populations and subsequently processed and sequenced to identify the TCRα and TCRβ chains of a single barcoded T cell.

In some embodiments, methods and devices are provided herein to isolate the particle bound cells (i.e., barcoded T cells). In some embodiments, the isolation is performed in microfluidic devices designed to isolate the barcoded T cells into individual single cell wells (e.g., individual wells of a multi-well plate), where they can be further processed and analyzed. In some embodiments, the barcoded T cells are isolated using FACS.

The devices and methods described herein can be used, for example to identify neoantigen-specific T cell populations, including their specific TCR chain pairing, from the tumor infiltrating lymphocytes (TILs) or peripheral blood mononuclear cells (PBMCs) of a cancer patient. In some embodiments, the analysis of such T cells and their respective TCR sequences informs the construction of personalized cancer vaccines or engineered-TCR T cell immunotherapies.

Barcoded Antigen-Mhc Particle Library Formation

A barcoded antigen-MHC library can be generated using particles, such as dextran (e.g., FIG. 1) or nanoparticles. The illustrated example in FIG. 1 is not to scale and each dextramer itself can be much larger than the DNA barcode trimers or the MHC-antigen trimers, so that each particle can in excess of 103 identical antigen-MHC complexes and DNA barcode trimers. Each library element is prepared separately, and designed so that each peptide antigen is associated with a unique defined barcode.

Particles

As used herein, "particles" refer to substrates capable of being specifically sorted or isolated, and to which other entities can be attached. The particle can be a nanoparticle. The particle can be fluorescent or attached to a fluorophore directly or indirectly.

The particle can be a dextran, such as a biotinylated dextran or streptavidin coated dextran. Modified dextrans are described in further detail in Bethune et al., *BioTechniques* 62:123-130 March 2017 and US Publication No. 2015/0329617, herein incorporated by reference in their entirety. MHC display moieties bound to streptavidin can be attached to biotinylated dextran. For example, an MHC display moiety can be an MHC trimer using a streptavidin core, wherein the streptavidin core is also bound to a fluorochrome.

The particle can be a bead. Examples of beads include, but are not limited to, agarose beads and sepharose beads. In some examples, the particle can be magnetic, e.g., for isolation using a magnet. The magnetic particle can comprises magnetic iron oxide. Examples of magnetic particles include, but are not limited, to Dynabeads™ (Thermo Fisher). The particle can also be a polystyrene particle, e.g., for isolation by gravity.

The particle can be modified with an attachment moiety for attaching additional elements, such as the DNA barcode trimers or the MHC-antigen trimers. Modification of the particle can include an attachment moiety that can pair with (e.g., covalently bind to) a corresponding cognate (e.g., complementary) attachment moiety, such as an attachment moiety attached to the DNA barcode trimers or the MHC-antigen trimers. Any suitable pair of attachment moieties may be used to modify the particle and the element for attachment. Non-limiting examples of attachment moiety pairs include a streptavidin/biotin system, a thiol group (e.g., cysteine) and maleimide, adamantane and cyclodextrin, an amino group and a carboxy group, and an azido group and alkynl group. The attachment moiety can comprise a cleavage moiety. The attachment moiety bound to complementary cognate attachment moiety can be reversible, such as a reducible thiol group.

In an exemplary system, the modified particle is a biotinylated dextran, the elements to be attached, such as the DNA barcode trimers or the MHC-antigen trimers, are biotinylated, and the biotinylated elements are bound to a streptavidin core, which is in turn attached to biotinylated dextran. In another exemplary systems, the modified particle is a streptavidin coated particle, such as 1 μm particles (e.g., Dynabeads™ MyOne™ Streptavidin T1 beads from ThermoFisher Scientific), and the elements to be attached, such as the DNA barcode trimers or the MHC-antigen trimers, are biotinylated and bound to the streptavidin coated particle.

Antigen-Mhc Complex

An antigen, for example each antigen in the barcoded antigen MHC particle library, can potentially be recognized by, and thus bind to, a specific population of T cells, by interacting with the T cell receptor. The antigen is prepared so that it can be recognized by the T cell receptor that defines the T cell population of interest. It is also prepared so that it is attached to a particle. In this way, once the antigen-specific T cells binds to the antigen, those T cells can be specifically isolated. An antigen can be a neoantigen. Computational analysis of a cancer patient's tumor genome can be used to define a series of candidate neoantigens used to build the barcoded antigen MHC particle library. Additional description of methods to identify neoantigens can be found in US Publication No. 2017/0003288.

An MHC display moiety can include a recombinant MHC molecule. The MHC display moiety can bind peptide antigens to form an antigen-MHC complex such that the antigens are capable of recognition by a cognate TCR molecule. The MHC complex can be an MHC Class I (MHC I) complex that pairs with CD8-positive (CD8+) T "killer" cells. The MHC complex can also be an MHC Class II (MHC II) complex that pairs with CD4+ "helper" T cells. The recombinant MHC molecule can be an MHC Class II molecule expressed and loaded with a candidate antigen peptide as described in Novak et al., 1999, *J. Clin. Invest.* 104:R63-R67, the entire contents of which are herein incorporated by reference. Additional description of types of MHC molecules that can be used are found in US Publication No. 2017/0003288. An MHC display moiety can comprise an attachment moiety, including the MHC display moiety being directly biotinylated.

The MHC display moiety can be a single chain trimer. Single-chain trimers are described in more detail in US Publication No. 2003/0003535, US Publication No. 2009/0117153, and US Publication No. 2008/0219947, each of which are incorporated by reference herein in its entirety. Briefly, as used herein, "single chain trimers" refer to recombinant MHC molecules expressed as a single polypeptide fusion of an antigen peptide, a β2-microglobulin, and a MHC class I heavy chain comprising the α1, α2, and α3 domains. In certain embodiments, single-chain trimers can comprise disulfide traps, as described in US Publication No. 2009/0117153 and US Publication No. 2008/0219947.

The MHC display moiety can be an MHC Class I molecule expressed with a conditional ligand. As the MHC class I molecule is unstable in the absence of peptide (i.e. antigen peptide), a recombinant MHC Class I molecule is expressed with a cleavable peptide, that upon irradiation with UV light dissociates from the complex and disintegrates. However, if the UV disintegration of the cleavable peptide is performed in the presence of a "rescue peptide," the rescue peptide will readily replace the UV irradiated peptide in the binding groove, as described in Toebes et al., 2006, *Nat. Med.* 12:246-251 and Bakker et al., *PNAS,* 2008, 105:3825-3830, the entire contents of both of which are herein incorporated by reference. Using this technology, several assembled MHC Class I molecules can be loaded with candidate antigens, including neoantigens, to form a MHC class I antigen library for screening T cells. The cleavable peptide can be replaced by the antigen of interest before the antigen-MHC complex is linked to the barcoded particle. An antigen-MHC complex can be linked to a barcoded particle with the cleavable peptide still bound to the MHC. This can be used to generate a library of barcoded particles with MHCs that can subsequently have the cleavable peptide released, e.g., the barcoded particle library irradiated, and replaced by an antigen of interest.

The MHC display moiety can be an MHC trimer complex of three MHC molecules, each loaded with the same candidate antigen. Since antigens, including neoantigens, can have low binding affinities ($K_d$) for MHC proteins (e.g., 500 nM or lower), a trimeric MHC complex allows for increased binding avidity, thereby increasing the sensitivity of the barcoded antigen-MHC particles for pairing with low abundance cognate T cells. The MHC trimer complex can be formed by three biotinylated MHCs bound to a streptavidin core, which in turn is bound to a particle, such as dextran. The MHC trimer complex can also be complexed with a fluorophore (also referred to as a fluorochrome). Fluorophore-MHC trimer dextran complexes (also referred to as "dextramers") are described in more detail in Bethune et al., *BioTechniques* 62:123-130 March 2017, herein incorporated by reference for all it teaches.

In some embodiments, an MHC display moiety is a tetramer complex of four MHC molecules each loaded with the same candidate antigen. In some embodiments, an MHC tetramer is formed using a cysteine-modified streptavidin ("SAC") conjugated with four biotin-modified MHC molecules.

Polynucleotide Barcodes

Embodiments can include a modified particle attached to barcoded polynucleotides comprising a defined barcode sequence. The barcoded polynucleotides can be a polynucleotide that provides a unique antigen-specific sequence for identification after T cell isolation. Therefore, each unique antigen-MHC complex is attached (i.e., hybridized) to a particle with a unique defined barcode sequence. This allows an operative association between a given antigen and a given barcode that is unique to the pair.

The barcoded polynucleotides can be ssDNA or dsDNA. The polynucleotides comprising the barcodes can be modified at their 5' end to comprise an attachment moiety for attachment to a particle. For example, the polynucleotides comprising the barcode sequences are conjugated to a biotin molecule for binding to a streptavidin-core attached to a particle, such as dextran. However, any suitable attachment moiety may be used for attachment of polynucleotides to a particle. As described herein and as understood by a person skilled in the art, suitable attachment moiety pairs are known in the art. Non-limiting examples of attachment moieties include thiol, maleimide, adamantane, cyclodextrin, amine, carboxy, azide, and alkyne.

In some embodiments, the polynucleotide sequences are modified at their 5' end to include a cleavage moiety. Subsequent to attachment of the polynucleotide sequences to a particle, the cleavage moiety allows for release of the barcoded polynucleotides from the particle. For example, following isolation of a T cell associated with the barcoded antigen-MHC complex, the barcoded polynucleotides can be cleaved (i.e., released) from the particle complex. In certain embodiments, the cleavage moiety is a photocleaveable moiety, such as UV cleavable moieties. An example of a UV cleavable linker is a biotin modification with a photocleavable group having the formula shown below ("5PCBio", synthesized by IDT):

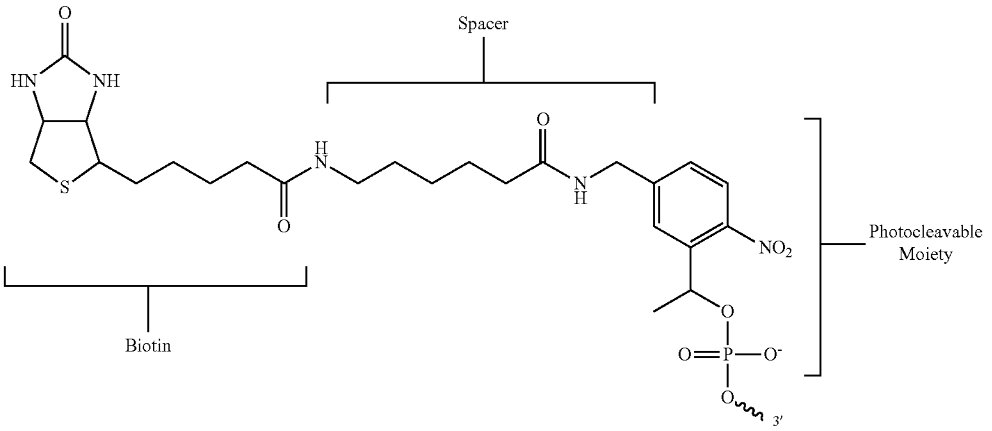

<http://www.idtdna.com/pages/education/decoded/article/which-biotin-modification-to-use->(retrieved Mar. 1, 2018)

In other embodiments, the cleavage moiety can comprise a reversible group, such as a reducible thiol group. Examples of cleavage moieties using reversible groups are described in US Publication No 2015/0376609, herein incorporated by reference.

When a barcoded antigen-MHC library element binds to a T cell, the particle complex is also attached to the T cell. Such a T cell is said to be 'barcoded.' All barcoded T cells can thus be separated from the other non-barcoded T cells fluorescence-activated cell sorting (FACS) techniques, such as when the particle or complex is fluorescent, or using magnetic separation techniques, if the particle is magnetic.

Purification of Antigen-Specific T Cells

Embodiments of the present invention include the use of a barcoded particle-antigen-MHC complex for screening antigen-specific T cells. As understood by a person skilled in the art, a single antigen may be assayed using the complex in the presence of T cells. However, assaying one candidate antigen is not as efficient as screening multiple candidate antigens.

Isolation and identification of patient-derived and antigen-specific T cells using a library of barcoded-antigen-MHC complexes can include incubating the candidate antigen complexes with patient-derived T cells. T cells can be prepared using standard methods that start from a tissue such as blood, a lymph node, or a tumor.

Patient-derived T cells can be isolated from the patient's peripheral blood mononuclear cells (PBMCs) or tumor infiltrating lymphocytes (TILs). For example, both CD4+ and CD8+ T cells can be labeled and sorted from PBMCs or TILS using anti-CD4 and anti-CD8 fluorescent antibodies, with live populations of CD4+ and CD8+ single-positive cells sorted using fluorescence-activated cell sorting (FACS), to isolate only CD4+ or CD8+ cells. In some embodiments, T cells that are positive for both CD4 and CD8 can be isolated using an anti-CD3 fluorescent antibody followed by FACS. A person skilled in the art is able to determine the type of T cells to isolate for the type or types of antigen-MHC complex being used.

Embodiments of the present invention include incubating a barcoded antigen-MHC complex library with a suspension of CD4+, CD8+ or CD4+/CD8+ T cells. Each library element is separately prepared, but then all library elements are combined and mixed with a single cell suspension of T cells.

Incubation of the particle library with the T cell suspension allows for a complete and thorough exposure of the particle-bound antigen to the various T-cell receptors. This method may include rocking or rotation of the cells.

Following incubation of the antigen complex and the T cells, the particle is selectively separated or selectively collected. Barcoded T cells will likely be bound to many identical copies of identical barcoded-antigen-MHC library elements, and can be separated based on these interactions. For example, if the particle complex contains a fluorophore, fluorescent associated cell sorting (FACS), including single-cell sorting, can be used to selectively isolate barcoded T cells. If the particle is magnetic, applying a magnet to the suspension can allow for separation of particles in a complex with antigen paired T cells and removal of unpaired T cells. Alternatively, if the particle is a polystyrene particle, the unpaired T cells may be separated by gravity (e.g., centrifugation). After removal of unpaired T cells, in some embodiments, the separated bound particles are washed at least once to remove any non-specifically associated T cells.

A full barcoded antigen-MHC library may include 5-1000 different antigens, each with their own DNA barcode ("NI"), although a 50-element library is typical. T cells can range from 8-20 micrometers in diameter. Each antigen-specific T cell can have many copies of an identical T cell receptor (TCR), so that an antigen-specific T cell can potentially be barcoded by many identical copies of a specific barcoded antigen-MHC library element.

For a sample of tumor infiltrating lymphocytes (TILs) or Peripheral Blood Mononuclear Cells (PBMCs) that contains $10^4$ CD8+ T cells, and for a (typical) barcoded antigen-MHC library size of 50, often between 5 and 200 T cells will be barcoded by between 1 and 15 of the 50 library elements. Because the T cell receptor interaction with the antigens is highly specific, each individual barcoded T cell will generally only be associated with a single library element, although multiple copies of that library element can (and will likely) be attached to the T cell. Each barcoded T cell will thus be associated with between 1-400 particles. In some examples, isolation of T cells requires multiple copies of that library element to be attached, e.g., for fluorescent complexes, wherein isolation generally requires a sufficient signal for isolation. In other embodiments, isolation requires binding to variations of the same barcoded-antigen-MHC complex with the same barcode, but other variations in the complex, e.g., different fluorophores, and isolation is determined by binding to fluorescent complexes with the same barcode (NI) and antigen but different fluorophores. Approximately $10^8$ particles, representing the 50 barcoded antigen-MHC library elements, might be mixed with the $10^4$ T cells in the barcoding process. Unbound barcoded antigen-MHC elements can outnumber the barcoded T cells by about 106:1 or more.

Fluorscence Activated Cell Sorting

Barcoded T cells can be sorted using fluorescence-activated cell sorting (FACS). Barcoded antigen-MHC complexes bound to a T cell can be made fluorescent using a variety of methods. For example, one or more of the attachment moieties can be fluorescent, such as a streptavidin core attached to or bound to a fluorescent molecule. In other examples, the T cell can be stained using antibodies conjugated to a fluorescent molecule, or in some examples stained using a panel of antibodies conjugated to different fluorescent molecules. In some examples, the particle can be fluorescent or conjugated to a fluorophore directly. In some embodiments, multiple elements within the complex (e.g., the attachment moiety, the stained T cell, and the nanoparticle) can be fluorescent, including each comprising a different fluorophore. The particles used can also be magnetic or non-magnetic. If magnetic, the particles can be separated using magnetic methods in conjunction with FACS, (e.g., before, after, or before and after FACS).

Individual barcoded T cells can be also separated by FACS into individual collection containers, such as a multiwell plate. The individual collection container can be single-cell reaction vessels. For example, components used for downstream processing and analysis can be added to each single-cell reaction vessel. The barcoded T cells can be separated by FACS into a bulk collection container (e.g., every barcoded T cell isolated is collected in the same container).

Barcoded T cells can also be individually isolated in droplets using a droplet generating microfluidic device (i.e., a "droplet generator"). Droplet generating devices used to encapsulate single cells are known to those skilled in the art, e.g., as described in US Publication No. 2006/0079583, US Publication No. 2006/0079584, US Publication No. 2010/0021984, US Publication No. 2015/0376609, US Publication No. 2009/0235990, and US Publication No. 2004/0180346.

T Cell Receptor Amplification and Analysis

Figure 2:
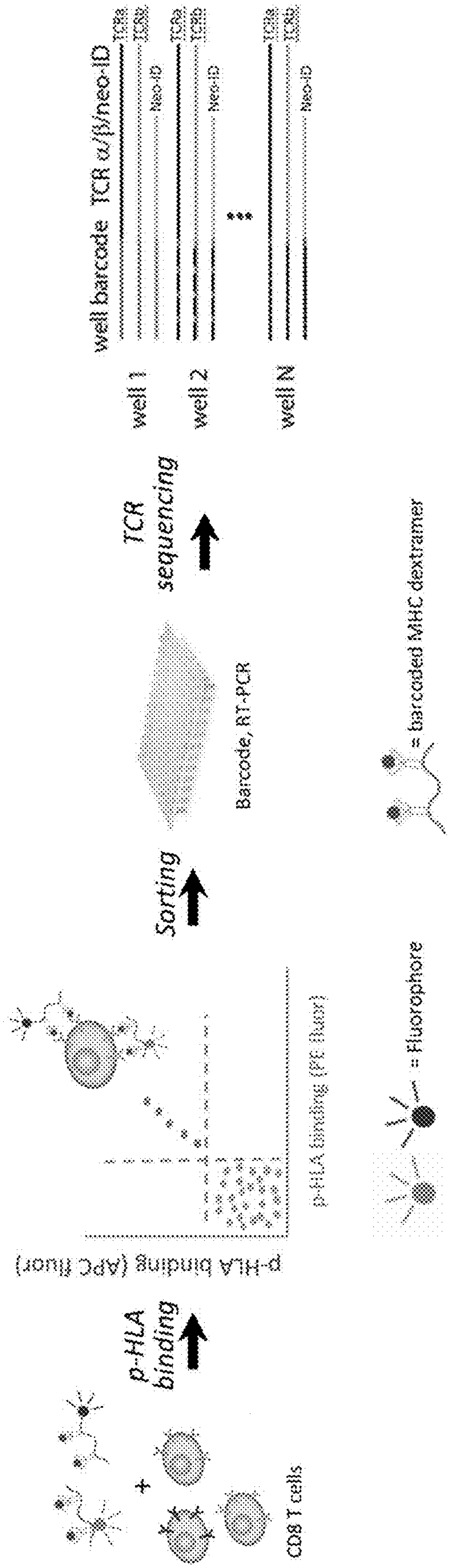
FIG. 2 illustrates an isolation scheme by single-cell sorting using dextramers (the composition and construction of the dextramers are shown in FIG. 1). As shown, fluorescently labeled barcoded MHC dextramers (i.e., the dextramers) are pooled together and used to stain CD8+ T cells followed by single-cell sorting by FACS into individual wells. Cells that demonstrate specific binding are selectively sorted based on binding to the same pair of unique DNA barcode trimers and MHC trimers attached to particles containing different fluorophores (i.e. dual labeled). Following sorting, primers are added for sequencing, such as primers specific for TCR-alpha and TCR-beta chains, as well as a unique well specific barcode to allow pairing of TCR-alpha and TCR-beta sequences with a specific antigen-MHC complex. RT-PCR is performed in the individual well to amplify the specific sequences of interest, followed by a nested PCR amplification. A third round of PCR adds the well specific barcode to the amplified DNA allowing pooling of multiple samples to be sent for sequencing in parallel.
Figure 4:
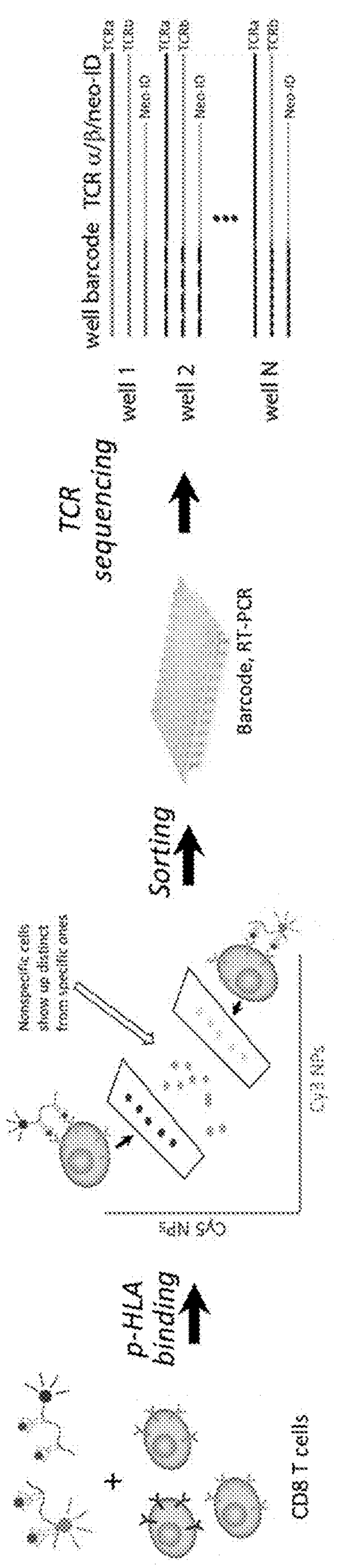
FIG. 4 illustrates an isolation scheme by single-cell sorting using dextramers (the composition and construction of the dextramers are shown in FIG. 1). As shown, fluorescently labeled barcoded MHC dextramers (i.e., the dextramers) are pooled together and used to stain CD8+ T cells followed by single-cell sorting by FACS into individual wells. Cells that demonstrate specific binding are selectively sorted based on binding to a unique DNA barcode trimer and MHC trimer associated with only a single fluorophore, where binding to multiple fluorophores connotes non-specific binding (i.e. singly labeled). Following sorting, primers are added for sequencing, such as primers specific for TCR-alpha and TCR-beta chains, as well as a unique well specific barcode to allow pairing of TCR-alpha and TCR-beta sequences with a specific antigen-MHC complex. RT-PCR is performed in the individual well to amplify the specific sequences of interest, followed by a nested PCR amplification. A third round of PCR adds the well specific barcode to the amplified DNA allowing pooling of multiple samples to be sent for sequencing in parallel.

After isolation of barcoded T cells into single-cell reaction vessels (e.g., isolated in individual well or droplets), the nucleic acid of the barcoded T cell can be further processed for downstream analysis. Specifically, the expressed TCRα and TCRβ mRNA transcripts can be first converted to cDNA by reverse transcription and the cDNA amplified for next generation sequencing. In general, as part of this process, the cDNA is barcoded with additional barcodes specific for each single-cell reaction vessels (e.g., each individual well or droplet) allowing downstream pairing of the TCRα and TCRβ mRNA transcripts with the specific antigen recognized by the T cell. The general scheme used to generate the barcoded TCRα and TCRβ cDNA specific for an antigen-MHC is illustrated in FIG. 2 and FIG. 4.

Following isolation of the single antigen specific T cell bound to one or more barcoded antigen-MHC complex, the transcripts for the expressed TCRα and TCRβ chains are converted to cDNA. To do so, the nucleic acid from the T cell can be released. For example, T cells can be lysed to release the nucleic acid. Examples of lysis agents include, but are not limited to lysis enzymes (e.g. lysozyme) and surfactants or detergents. In certain embodiments, the surfactant is a non-ionic surfactant including, but not limited to, IGEPAL CA 630, TritonX-100, and Tween 20. In other embodiments, the surfactant is an ionic surfactants including, but not limited to, sarcosyl and sodium dodecyl sulfate (SDS). Non-reagent based lysis systems can also be used to release nucleic acid from a cell including, but not limited to, heat, electroporation, mechanical disruption, and acoustic disruption (e.g., sonication).

Following release of the nucleic acid (e.g., the TCRα and TCRβ mRNA transcripts) from the cell into the single-cell reaction vessel, mRNA is reverse transcribed into cDNA. In general, reverse transcriptase (RT) and primers specific for genes of interest are added directly to a single-cell reaction vessel. RT and primers can be added simultaneously with other reagents (e.g., the lysing, releasing, and PCR amplification reagents described elsewhere). In addition to the RT and primers, additional components are generally added to carry out the first strand synthesis of cDNA. Examples of additional components are well known to those skilled in the art and include, but are not limited to, dNTPs, RNase inhibitors, buffering agents (e.g., Tris-HCL), chelators (e.g., EDTA), and DTT. In specific examples, the additional components, such as DTT, are added to increase efficiency of the RT reaction. In preferred embodiments, the final DTT concentration is 5 mM.

To generate cDNA from mRNA, a single-stranded DNA polynucleotide (e.g., the "primer") anneals to the mRNA and reverse transcriptase transcribes the first strand cDNA using the mRNA as a template. In specific examples, TCRα and TCRβ primer sequences are used and act as the initial primers by annealing to regions of the TCRα and TCRβ constant region sequences of TCRα and TCRβ mRNA transcripts, respectively. Primers for other genes of interest can also be added (e.g., CD8 or PD-1).

In general, following cDNA first strand-synthesis, additional PCR amplification are performed. In some examples, additional amplification primers, as well as any reagents necessary for further PCR amplification, can be added prior to reverse transcription. In other examples, additional amplification primers, as well as any reagents necessary for further PCR amplification, can be added following reverse transcription. Additional amplification primers, as well as any reagents necessary for further PCR amplification, can be added directly to a single-cell reaction vessel.

Additional primers can comprises polynucleotides including, but are not limited to, well-specific barcode sequence, universal sequencing adaptors (e.g., Illumina adaptors), a unique molecular identifier ("UMI"), or combinations thereof.

A well-specific barcode sequence, as used herein, is a polynucleotide sequence that allows for operatively associating a given sequence and a specific single-cell reaction vessel (e.g., each individual well or droplet), during subsequent sequencing analysis. For example, well-specific barcode sequence can be used to pair a TCRα sequence, a TCRβ sequence, a specific antigen-MHC complex (i.e., the barcode sequence unique to the specific antigen-MHC), and any other sequence of with a single-cell (e.g., a barcoded T cell) isolated in an individual well.

A UMI, as used herein, is a random nucleotide sequence that is, in principal, unique for every individual polypeptide. UMIs are useful in downstream sequencing analysis, specifically single-cell sequencing analysis, to remove sequencing errors due to amplification bias of certain sequences and is well known to those skilled in the art, for example, as described in further detail in Islam et al. (Nature Methods volume 11, pages 163-166; 2014), herein incorporated by reference in its entirety.

Following amplification of the barcoded amplification products, including cDNAs, and attachment of sequencing adaptors, the barcoded amplification products are sequenced using next generation sequencing (NGS) methods known to those skilled in the art, including, but not limited to, sequencing by synthesis technologies (Illumina). Once sequenced, the resulting sequencing reads can be analyzed and the defined barcode sequence (i.e., the barcode used to pair antigen specific TCRα and a TCRβ chains, or other genes of interest, with a barcoded T cell.

Examples

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* 3rd Ed. (Plenum Press) Vols A and B (1992).

Example 1: Generation of Antigen-MHC HLA Polypeptides

Antigen-presenting HLA polypeptides (i.e., antigen-MHCs) comprise a single polypeptide consisting (from amino to carboxy terminus) of a secretory protein leader sequence (to direct the polypeptide into the endoplasmic reticulum of the secretory pathway) covalently linked to each individual candidate antigenic peptide, which is covalently linked to the light chain B2 microglobulin polypeptide and covalently linked to the heavy chain of the HLA class I receptor (unique to each HLA class I allele), also referred to as a single chain trimer. Single-chain trimers are described in more detail in US Publication No. 2003/0003535, US Publication No. 2009/0117153, and US Publication No. 2008/0219947, each of which are incorporated by reference herein in its entirety. Single-chain trimers may comprise disulfide traps, as described in US Publication No. 2009/0117153 and US Publication No. 2008/0219947, each of which are incorporated by reference herein in its entirety. The antigen-presenting HLA polypeptide is further covalently linked to a polyvalent purification and binding cluster sequence, which includes a biotinylation recognition sequence (for binding to streptavidin) plus TEV protease cleavage recognition sequence plus a 6×His tag sequence to support purification of each entire polypeptide on nickel affinity binding columns. The system allows production of patient-specific reagents at the DNA level instead of at the peptide level, thereby accelerating reagent production to support personalized "just-in-time" product development processes. The DNA encoding each antigen-presenting HLA polypeptide is transfected into Expi293F mammalian cells to express and to secrete the polypeptide into the media for subsequent purification. This process yields biotinylated, soluble and well folded polypeptides that serve as molecular baits to bind their cognate TCR. Specific antigens of interest tested are neoantigens (also referred to as "NeoE" peptides).

Example 2: Assembly and Use of Avidity Binding Components

Two alternative types of avidity binding components (i.e., a barcoded antigen-MHC complex or library element), dextramers (FIG. 1) and nanoparticles, comprising antigen-presenting HLA polypeptides together with DNA barcodes have been developed. The multimeric assembly of antigen-presenting HLA polypeptides translates the weak binding affinity of individual antigen-presenting HLA polypeptide by their cognate TCRs to be overcome with increased binding avidity. The specific labeling of each individual avidity binding element with its own DNA barcode links T cell binding of individual antigen-presenting HLA polypeptides to the antigen identity after isolation.

To accommodate different HLA alleles expressed by the spectrum of cancer patients, a diverse repertoire of HLA polypeptide templates encoding ~50 most common HLA class I heavy chain segments have been generated (Table 1). Additional alleles are added to the repertoire of HLA polypeptide templates as needed.

To build a high-throughput approach for producing antigen-presenting HLA polypeptides against multiple antigen candidates for the different alleles of each patient, a "mini-gene" approach is developed where linear amplicons encoding all the cis-elements required for transcription and translation are used for mammalian cell transfection. This approach involves the use of individual coding DNA from PCR amplification without the need for passage through and purification of plasmid DNA from *E. coli* for transfection. Mini-genes contain a CMV promoter and a Human Growth Hormone signal/leader sequence to direct the polypeptide into the secretory pathway. The antigen coding sequence is flanked by two restriction sites for directional cloning. The MHC is a heavy chain of HLA class I receptors and is variable depending of the individual patient Haplotype. An Avitag sequence code for the motif GLNDIFEAQKIEWHE (SEQ ID NO: 2) allow for specific biotinylation by the BirA biotin Ligase. A 6×His is necessary for affinity purification. A BGH pA tagged is the non-coding sequence Bovine Growth Hormone polyadenylation site.

TABLE 1

COMMON HLA CLASS I HEAVY CHAIN SEGMENTS

| HLA-A | HLA-B | HLA-C |
|---|---|---|
| HLA-A*01:01 | HLA-B*07:02 | HLA-C*01:02 |
| HLA-A*02:01 | HLA-B*08:01 | HLA-C*02:02 |
| HLA-A*03:01 | HLA-B*13:02 | HLA-C*03:03 |
| HLA-A*11:01 | HLA-B*14:02 | HLA-C*03:04 |
| HLA-A*23:01 | HLA-B*15:01 | HLA-C*04:01 |
| HLA-A*24:02 | HLA-B*15:03 | HLA-C*05:01 |
| HLA-A*25:01 | HLA-B*15:07 | HLA-C*06:02 |
| HLA-A*26:01 | HLA-B*18:01 | HLA-C*07:01 |
| HLA-A*29:02 | HLA-B*27:02 | HLA-C*07:02 |
| HLA-A*30:01 | HLA-B*27:05 | HLA-C*07:04 |
| HLA-A*30:02 | HLA-B*35:01 | HLA-C*08:01 |
| HLA-A*31:01 | HLA-B*35:03 | HLA-C*08:02 |
| HLA-A*32:01 | HLA-B*37:01 | HLA-C*12:02 |
| HLA-A*33:01 | HLA-B*38:01 | HLA-C*12:03 |
| HLA-A*33:03 | HLA-B*39:01 | HLA-C*14:02 |
| HLA-A*68:01 | HLA-B*40:01 | HLA-C*15:02 |
| HLA-A*68:02 | HLA-B*40:02 | HLA-C*16:01 |
| | HLA-B*41:02 | HLA-C*17:01 |
| | HLA-B*42:01 | |
| | HLA-B*44:02 | |
| | HLA-B*44:03 | |
| | HLA-B*44:05 | |
| | HLA-B*46:01 | |
| | HLA-B*49:01 | |
| | HLA-B*50:01 | |
| | HLA-B*51:01 | |
| | HLA-B*52:01 | |
| | HLA-B*53:01 | |
| | HLA-B*55:01 | |
| | HLA-B*57:01 | |
| | HLA-B*58:01 | |

Example 3: Molecular Analysis of Antigen-Specific T Cells

Using either dextramers or nanoparticles, the bound antigen-specific CD8 T cells are separated from other cells by fluorescence activated cytometry cell sorting (FACS) as single cells into individual wells of a 96 well plate, where each well contains cell lysis buffer. The cellular mRNA in each well is independently amplified by reverse-transcription then via polymerase chain reaction, followed by bulk sequence analysis via next generation sequencing. Separate PCR reactions on the combined DNA and complementary DNA from cells allow determination of TCRα and TCRβ sequences, the identity of the cognate antigen, as well as several phenotypic T cell markers to assess whether the corresponding T cell had been previously activated in connection with antigen exposure (antigen-experienced antigen-specific T cell).

Example 4: Barcodes Unique to an Antigen-MHC

Figure 6:
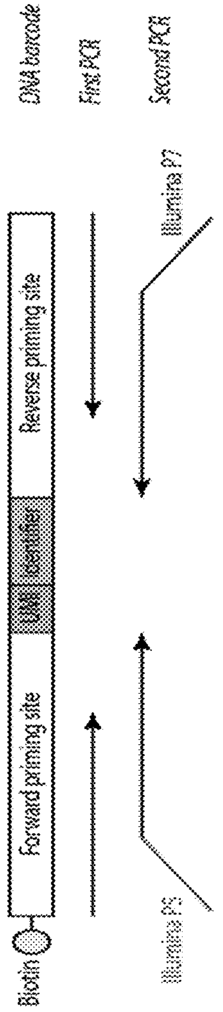
FIG. 6 illustrates a schematic of an antigen-specific DNA barcode.

Dextramers and nanoparticles have covalently linked DNA barcode sequences to identify the antigen specificity of each isolated CD8 T cell. As shown in FIG. 6, the antigen barcode comprises a biotinylated oligonucleotide with forward and reverse priming sequences to facilitate nested PCR of the internal sequence segment. The internal segment encodes a variable identifier sequence different for each element of the dextramer library or nanoparticle library. It also encodes a universal molecular index (UMI), which is a stretch of nucleotides synthesized using a mixture of all four bases at each position. Each UMI thus constitutes a unique molecular tag sequence per barcode as an independent tracking system to detect and to quantify the sequences associated with any particular identifier sequence.

During molecular analysis of an isolated cell, two rounds of PCR are performed to amplify the antigen-specific barcodes bound to the cell. The second round of PCR attaches standard Illumina adapters to the barcode sequence, so that a third round of PCR attaches row and column barcodes (i.e., a well-specific barcode sequence) that allow multiplexing of samples for next-generation sequencing.

The UMIs in the antigen-specific barcode confers unique tagging of each barcode molecule initially bound to the cell of interest. Therefore, by counting the number of UMIs associated with each identifier sequence in the NGS data, the number of dextramers or nanoparticles of each library element bound to the cell of interest is defined.

Example 5: MHC-Antigen Dextramer and Nanoparticle Production

Soluble monomeric MHC/peptide complexes have been produced to enable the study of TCR-MHC binding. However, the affinity of these monomeric binding is in the range of μM, which failed to yield a stable TCR-MHC complex (i.e., a barcoded T cell).

In one approach to solve this problem, an MHC trimer complex of three MHC molecules, each loaded with the same candidate antigen, is formed by three biotinylated MHCs bound to a streptavidin core. The MHC trimer complex is bound to dextran and is also be complexed with a fluorophore (also referred to as a fluorochrome). Fluorophore-MHC trimer dextran complexes (also referred to as "dextramers") are described in more detail in Bethune et al., *BioTechniques* 62:123-130 March 2017, herein incorporated by reference for all it teaches. Specifically, the MHC trimer is formed by incubating 3 equivalent of a biotinylated antigen-presenting HLA polypeptide with 1 equivalent of fluorescent streptavidin, leaving the streptavidin with one binding pocket. To barcode each antigen-presenting HLA polypeptide library element, a DNA-barcode trimer is also formed by incubating 3 equivalent of a biotinylated unique DNA oligo (the antigen-specific barcode) and with 1 equivalent of fluorescent streptavidin, also leaving the streptavidin with one binding pocket. To generate the final dextramer (i.e., the antigen-presenting HLA polypeptide library element), the DNA barcode trimer and the MHC trimer are mixed together and then added to biotin-dextran. The same pair of unique DNA barcode trimers and MHC trimers may also be mixed with streptavidins containing different fluorophores. The prepared dextramers are pooled together to form the library for patient sample analysis.

In another approach to solve this problem, a barcoded nanoparticle is generated, such as an MHC tetramer formed using modified streptavidin conjugated with four biotin-modified MHC molecules.

Example 6: Capture of Antigen-Specific T Cells Using Dextramer or Nanoparticles Patient PBMCs and healthy donor PBMCs are doped with T cells with a known TCR as an internal positive control to validate the entire analysis process. These cells are then stained with the pooled dextramer or nanoparticle library and other cell markers for FACS analysis.

First, the healthy donor PBMC is analyzed to define the gating strategy. Next, the patient sample is analyzed with the same gating strategy.

Antigen-specific T cells, internal positive cells, and non-specific T cells are stained by fluorescent dextramers or nanoparticles and sorted as single cells into plates for subsequent RT-PCR analysis.

In some cases, antigen-specific T cells are identified by fluorescence where an antigen-specific T cell is considered a specific binder only if the T cell binds to the same pair of unique DNA barcode trimers and MHC trimers attached to particles containing different fluorophores (i.e. dual labeled, FIG. 2).

In some cases, antigen-specific T cells are identified by fluorescence where an antigen-specific T cell is considered a specific binder only if the T cell binds to a unique DNA barcode trimer and MHC trimer associated with only a single fluorophore, where binding to multiple fluorophores connotes non-specific binding (i.e. singly labeled, FIG. 4).

Example 7: Single-Cell Sequencing

Figure 7:
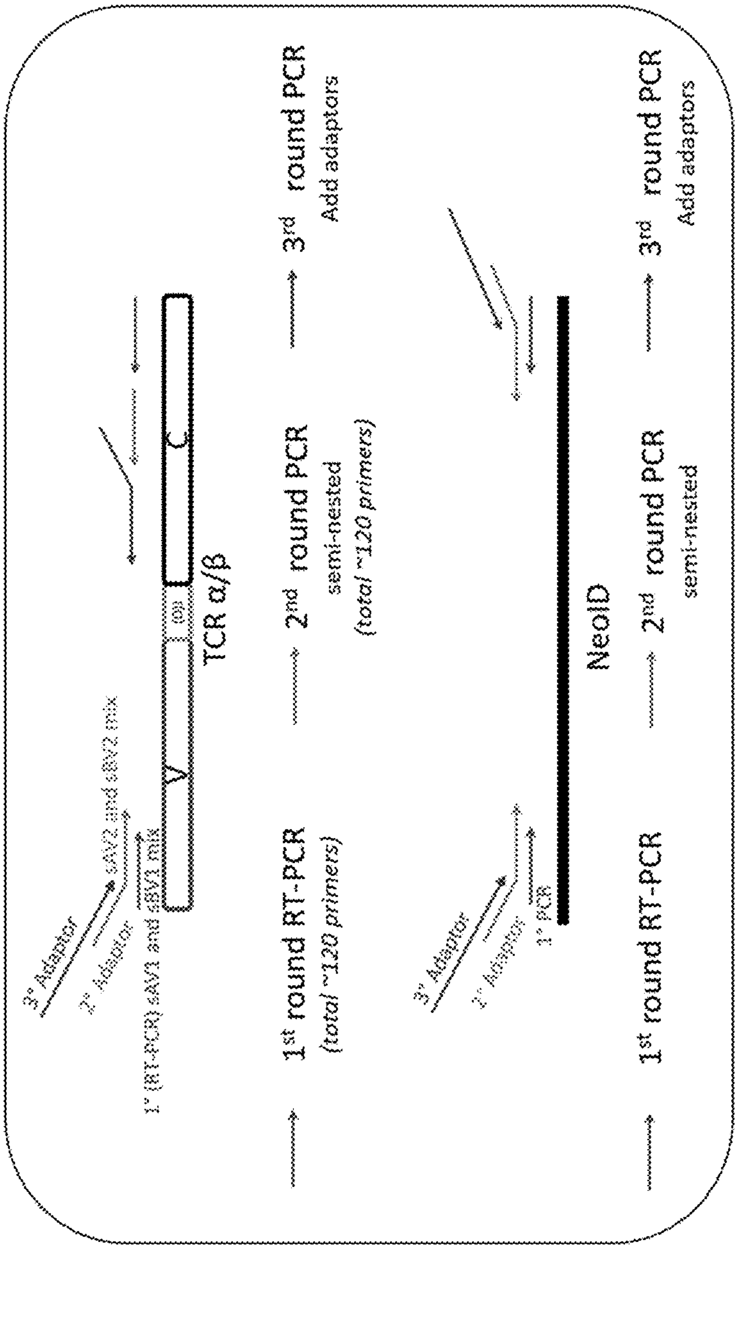
FIG. 7 illustrates a PCR schematic useful for single-cell sequencing of antigen-specific T cells.
Figure 8:
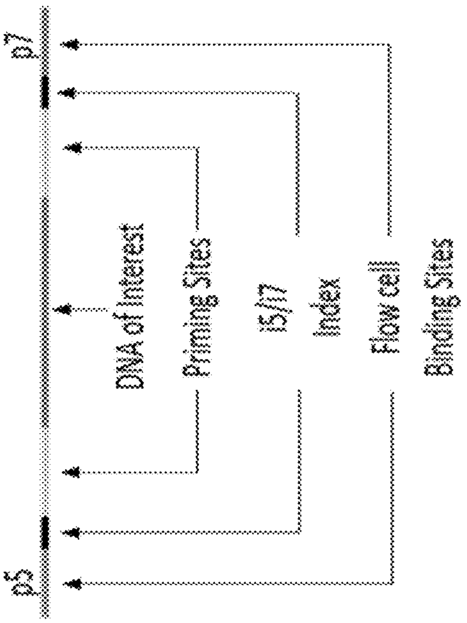
FIG. 8 illustrates an exemplary amplified DNA for single-cell sequencing of antigen-specific T cells (left), and an example of a well-specific primer layout (right).

Following single-cell sorting into individual wells of a multi-well plate, each single cell is lysed and subjected to an RT-PCR reaction. A fraction of the RT-PCR product is utilized to initiate another two rounds of PCR reaction to further amplify the TCR alpha and beta chains, amplify antigen-specific DNA barcodes, and attach the Illumina adaptors for sequencing, an overview of which is shown in FIG. 7. Single-cell amplified DNA are sequenced by Illumina Miniseq sequencing system. As illustrated in FIG. 8, the structures of the amplified DNA are as following: 1) p5 and p7 adaptors allows the DNA to bind to the Illumina flow cell; 2) i5 and i7 sequences barcode the physical 96-well position of the PCR products, for instance, DNA with i503 and i703 barcode is from well C3; 3) priming sites bind to the Illumina primer to initiate the sequencing read, 4) Sequences of interest are the TCR alpha and beta chains or antigen-specific barcode. After sequencing, each well contains amplified DNA sequences for TCR alpha and beta chains and the antigen-specific barcode, each containing a well-specific barcode.

After sequencing is completed, FASTQ files are inputted into the TCR analysis pipeline applying software program: MiXCR (version 2.1.3) with the parameters set for RNA-Seq sequencing using human TCR from IMGT as reference. Briefly, first, the raw reads are aligned to references to generate the scaffold, then 3 rounds of assembling and calibrations are completed to rescue imperfect reads caused by rearrangement at CDR3 regions. The final alignment is made to extend the match to ensure accuracy and sensitivity.

After this process, CDR3 nucleotide and amino acid sequences are identified, and TCR α and β V and J genes and anchor sites are determined. The reads for TCR α and β chains are exported from alignment together with the read counts, CDR3, and V and J genes of each unique read for TCR reconstruction. The reads containing adaptors, barcode/UMI sequences are tallied for each well, and the 6-nucleotide UMIs following each barcode are summed. Each unique barcode-UMI combination is collapsed to one to calculate each barcode's counts of occurrence for each well.

Subsequent TCR α and β analyses are done well-based. The corresponding CDR3s of each well are filtered to only include CDR3 containing reads from previously exported reads for further analyses. Based on the CDR3, V gene, J gene, and anchor sites from MiXCR analysis, the V gene and J gene sections are extracted from reads, and reference V gene or J gene with exact matches to these reads' sections are selected to reconstruct putative TCRs with the CDR3 sequence.

Figure 3:
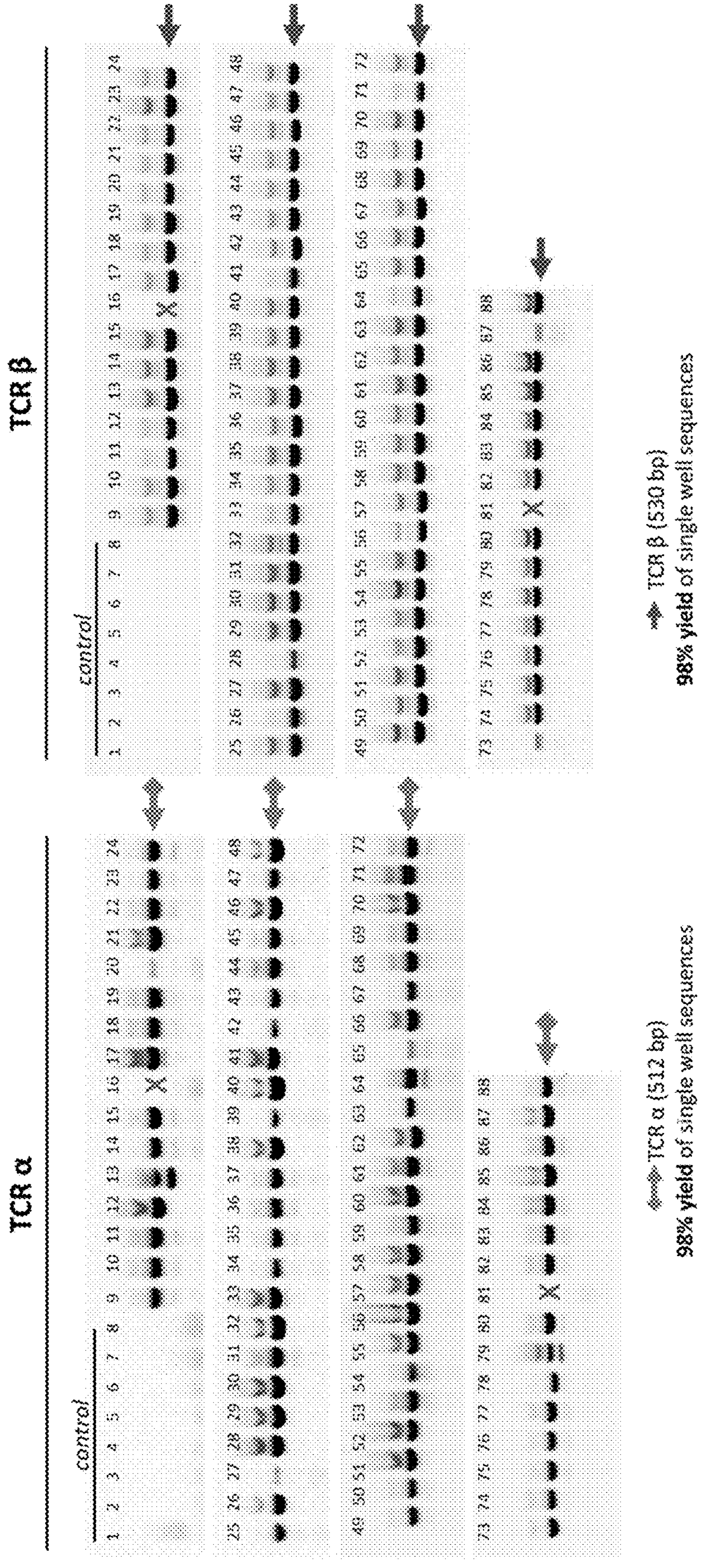
FIG. 3 shows exemplary RT-PCR and DNA amplification results of TCR identification using single-cell sorting methods. As shown in the figure, p-HLA: NLVPMVATV (SEQ ID NO: 1).

An exemplary isolation and subsequent sequencing analysis of antigen-specific TCR identification was performed using dextramers. Single-cell sorting and subsequent DNA amplification was also performed. As shown in FIG. 3, DNA amplification was observed for TCR α and β transcripts. As shown in Table 2, individual clonotypes specific for an antigen-MHC were identified.

TABLE 2

CLONOTYPES OF SINGLE CELL ISOLATED TCR SEQUENCES

| Clone | # of isolated clone-specific T cells* | % of epitope-specific T cells |
|---|---|---|
| 1 | 43 | 67.2 |
| 2 | 5 | 7.8 |
| 3 | 4 | 6.3 |
| 4 | 2 | 3.1 |
| 5 | 2 | 3.1 |
| 6-13 | 1 each | 1.6 each |

*64 (80%) of single T cells yield complete TCR (α and β) sequences

As shown in Table 2, the clonotypes of single cell isolated TCR sequences reveals the diversity of the epitope-specific T cell response. Furthermore, following bioinformatic analysis & selection, one of the TCRs identified in Table 2 can then be used for cloning, T cell engineering, and characterization for GMP TCR-T cell product manufacturing. This provides a method of making a TCR-T cell product of GMP quality for the treatment of patients with a cellular disease in need of cellular therapy. This also provides a method of making a TCR-T cell product of GMP quality for the treatment of cancer and patients with cancer in need of such treatment.

Figure 5:
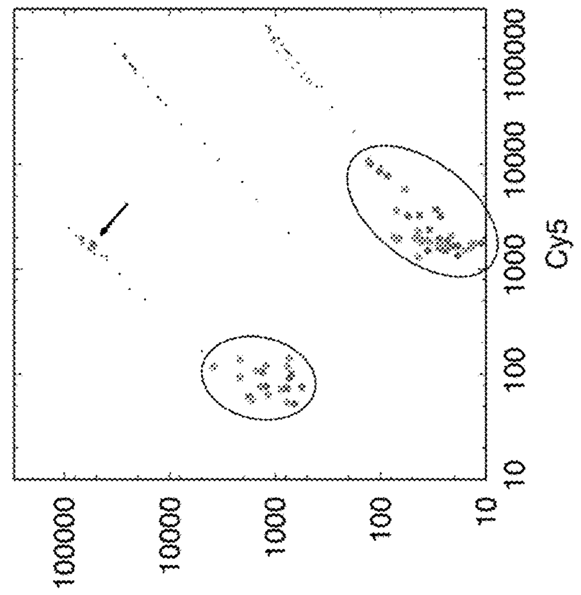
FIG. 5 shows an exemplary FACS sorting analysis using nanoparticles. Small dots represent cells from control sample used to distinguish specific and non-specific labeling. Large dots (circled and indicated by arrow) represent cells from a patient sample that demonstrated specific labeling and were sorted onto a PCR plate(s).

An exemplary isolation was also performed using nanoparticles. Cells were selectively sorted based on binding to nanoparticle populations with only a single fluorophore, where binding to multiple fluorophores connoted non-specific binding. As shown in FIG. 5, T cells specific for antigen-MHCs was separated from T cells with non-specific binding.

Example 8: Identification of TCR Sequences Specific for Neo-Antigens

The above methods are used to identify neo-antigen specific TCR sequences. Specifically, a library containing barcoded antigen-MHC dextramers and nanoparticles displaying potential neoantigens is prepared, with each antigen associated with a unique antigen-specific HLA barcode. For identification of a patient's putative neoantigens (tumor or pathogen), in silico predictive algorithmic programs are utilized that analyze the tumor, viral, or bacterial sequencing data to identify somatic mutations corresponding to putatively expressed neoantigens. Additionally, human leukocyte antigen (HLA) typing is determined from a tumor or blood sample of the patient, and this HLA information is utilized together with the identified putative neoantigen peptide sequences in a predictive algorithm for MHC binding, as verified by Fritsch et al., 2014, *Cancer Immunol Res.*, 2:522-529, the entire contents of which are herein incorporated by reference. Additional description of methods to identify neoantigens can be found in US Publication No. 2017/0003288. These in silico analyses result in a ranked list of the patient's candidate neoantigen peptides which can be readily synthesized for screening of cognate antigen-specific T cells. Once the list is generated, the candidate peptides are synthesized and of a library of barcoded antigen-MHC complexes displaying the candidate peptides is produced. The library is mixed with patient samples containing potential neoantigen-specific T cells. Barcoded T cells are separated and isolated by single-cell FACS sorting, and cDNA libraries are generated and sequences, as described above. The sequences are analyzed, and paired neoantigen-specific TCRα and TCRβ sequences are identified.

Other Embodiments

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A method for sorting and isolating an antigen-specific T cell, the method comprising:

a) contacting a sample with a library of barcoded particles in conditions sufficient for a T cell to bind the particles, wherein each of said particles comprises:

(i) a plurality of first streptavidin cores, wherein each core comprises a fluorophore, each core bound to three MHC-antigen trimer complexes, wherein each of the three MHC-antigen trimer complexes comprises an MHC molecule loaded with the same antigen; and (ii) a plurality of second streptavidin cores, wherein each core comprises a fluorophore, each core bound to three DNA barcodes, wherein each of the three DNA barcodes comprises a polynucleotide comprising a barcode associated with the identity of the antigen; and b) isolating an antigen-specific T cell, wherein the library comprises barcoded particles with two or more distinct fluorophores, and the antigen-specificity of the T cell is determined by sorting for fluorescence.

2. The method of claim 1, wherein the particle is selected from the group consisting of magnetic particles, agarose particles, sepharose particles, styrene polymer particles, and dextran polymer particles.

3. The method of claim 2, wherein the particle is a dextran polymer particle.

4. The method of claim 1, wherein the particle is streptavidin-coated.

5. The method of claim 1, wherein the antigen is a neoantigen.

6. The method of claim 1, wherein the polynucleotide comprises a cleavage moiety.

7. The method of claim 1, wherein each of the MHC molecule is an MHC Class I molecule or an MHC Class II molecule.

8. The method of claim 7, wherein the MHC Class I molecule is selected from the group consisting of HLA-A, HLA-B, and HLA-C.

9. The method of claim 7, wherein the MHC Class II molecule is HLA-DQ or HLA-DR.

10. The method of claim 1, wherein the sample is selected from the group consisting of blood, plasma, a peripheral blood mononuclear cell population, a tissue homogenate, a tumor homogenate, and an ex vivo T cell culture.

11. The method of claim 1, wherein the T cell is selected from the group consisting of a primary T cell, an ex vivo cultured T cell, a tumor-infiltrating T cell, and an engineered T cell.

12. The method of claim 1, wherein isolating comprises single-cell sorting.

13. A method for identifying TCR sequences of an antigen-specific T cell, the method comprising:

a) contacting a sample with a library of barcoded particles in conditions sufficient for a T cell to bind the particles, wherein each of said particle comprises:

(i) a plurality of first streptavidin cores, wherein each core comprises a fluorophore, each core bound to three MHC-antigen trimer complexes, wherein each of the three MHC-antigen trimer complexes comprises an MHC molecule loaded with the same antigen; and (ii) a plurality of second streptavidin cores, wherein each core comprises the fluorophore, each core bound to three DNA barcodes, wherein each of the three DNA barcodes comprises a polynucleotide comprising a barcode associated with the identity of the antigen;

b) isolating an antigen-specific T cell, wherein the library comprises barcoded particles with two or more distinct fluorophores, and the isolating comprises gating and sorting the T cells based on the detection of two of more distinct fluorophores within the sample; and c) obtaining the TCR sequences.

14. The method of claim 13 further comprising amplifying a TCR alpha gene sequence and a TCR beta gene sequence.

15. The method of claim 13, wherein the T cell is isolated in a single-cell reaction vessel.

* * * * *